United States Patent [19]

O'Boyle

[11] Patent Number: 4,874,386

[45] Date of Patent: Oct. 17, 1989

[54] FLUID DISPENSING DEVICE

[75] Inventor: Matthew O'Boyle, Houston, Tex.

[73] Assignee: STA-SET Corporation, Houston, Tex.

[21] Appl. No.: 49,940

[22] Filed: May 15, 1987

Related U.S. Application Data

[63] Continuation-in-part of Ser. No. 938,620, Dec. 5, 1986, Pat. No. 4,822,344.

[51] Int. Cl.[4] ............................................. A61D 5/005
[52] U.S. Cl. ..................... 604/246; 604/135; 604/248
[58] Field of Search ........................... 604/93, 131–135, 604/138–141, 143, 246, 248; 138/43, 46, 40; 210/437

[56] References Cited

U.S. PATENT DOCUMENTS

| | | | |
|---|---|---|---|
| 2,833,311 | 5/1958 | Baldelli | 138/43 |
| 3,532,126 | 10/1970 | Boothe | 138/43 |
| 3,877,428 | 4/1975 | Seagle et al. | 138/46 |
| 4,011,893 | 3/1977 | Bentley | 138/43 |
| 4,275,767 | 6/1981 | Westfall | 138/40 |
| 4,298,000 | 11/1981 | Thill et al. | 128/218 A |
| 4,351,335 | 9/1982 | Whitney et al. | 128/218 A |
| 4,447,232 | 5/1984 | Sealfon et al. | 604/134 |
| 4,507,115 | 3/1985 | Kambara et al. | 604/131 |
| 4,537,680 | 8/1985 | Barth | 210/437 |
| 4,626,244 | 12/1986 | Reinicke | 604/891 |
| 4,634,434 | 1/1987 | Marino, Jr. et al. | 604/246 |

FOREIGN PATENT DOCUMENTS

| | | |
|---|---|---|
| 168675 | 1/1986 | European Pat. Off. . |
| 2091189 | 5/1971 | France . |

OTHER PUBLICATIONS

"Low-Compliance Perfusion Pump for Oesophagael Manometry", P. Ask, *Medical & Biological Engineering & Computing*, Nov. 1978, pp. 732–738, vol. 16.

*Primary Examiner*—C. Fred Rosenbaum
*Assistant Examiner*—Kathleen A. Daley
*Attorney, Agent, or Firm*—Fitch, Even, Tabin & Flannery

[57] ABSTRACT

A fluid dispensing device useful as an inexpensive, lightweight ambulatory disposal drug infusion pump comprises a flexible reservoir for liquid to be administered parenterally to a patient, a mechanism for placing the liquid in the reservoir under a constant pressure for dispensing the liquid from the device, a distal septum for introducing liquid in the reservoir, and a flow control mechanism for adjustably controlling the flow rate of the liquid dispensed from the device.

16 Claims, 6 Drawing Sheets

FLUID DISPENSING DEVICE

REFERENCE TO RELATED APPLICATION

This application is a continuation-in-part application of U.S. application Ser. No. 938,620 filed Dec. 5, 1986, now U.S. Pat. No. 4,822,344, the disclosure of which is hereby incorporated by reference.

BACKGROUND AND SUMMARY OF THE INVENTION

The present invention is directed to a fluid dispensing device for administering liquid parenterally to a patient. More particularly, the invention relates to a fluid dispensing device useful as an ambulatory disposable drug infusion pump for accurately controlling the liquid administered parenterally to a patient.

Ambulatory drug infusion devices are known. Typically, such devices are sophisticated, computer controlled, electrically operated pumps which permit a patient to continuously receive a drug as an outpatient. The cost of these devices is great thus limiting their application.

An object of the present invention is to provide an improved ambulatory drug infusion device which is inexpensive, light-weight and disposable. A further object of the invention is to provide an improved ambulatory drug infusion device which is not operated electrically thereby avoiding the necessity of batteries, etc.

These and other objects of the invention are attained by the fluid dispensing device of the invention which comprises a reservoir for a liquid to be administered parenterally to a patient, means for placing the liquid in the reservoir under a constant pressure for dispensing the liquid from the device, and flow control means for adjustably controlling the flow rate of the liquid dispensed from the device. The flow control means according to the preferred embodiment of the invention comprises an elongated passage through which liquid from the reservoir can be flowed to an outlet of the device and means for changing the length of the elongated passage through which the liquid is flowed thereby changing the flow rate of the liquid through the passage. In the disclosed embodiments of the invention, the means for placing the liquid in the reservoir under a constant pressure for dispensing the liquid from the device comprises a spring and means for tensioning the spring once the reservoir has been filled with liquid through A means of the device for introducing liquid in the reservoir.

More particularly, according to the disclosed embodiments, at least a portion of the reservoir is formed of a flexible material to allow the reservoir to be compressed to place the liquid therein under pressure and to collapse the reservoir as the liquid is dispensed from the device. The means for placing the liquid in the reservoir under a constant pressure presses the flexible material of the reservoir to place the liquid therein under constant pressure. According to a preferred embodiment of the invention, the means for placing the liquid in the reservoir under a constant pressure comprises a compression spring and a variable helix angle translator interposed between the compression spring and the reservoir of the device, so that a constant force can be applied to the liquid in the reservoir as the compression spring extends in order to maintain the constant pressure on the liquid in the reservoir. A spring load adjuster means is provided in the device to permit adjustment of the position of the compression spring during assembly of the device to compensate for any variations in the load rate of the spring from a desired, predetermined load rate. A second embodiment of the invention comprises a constant load negator type spring and means translating a radial force of the spring into axial force for application to the liquid in the reservoir as the means for placing a constant pressure on the liquid in the reservoir.

The means defining an elongated passage in the flow control means includes a metering member having an elongated groove with a small cross-sectional area formed in a first surface thereof and a baffle member having a surface overlying the groove to form the elongated passage. The means for changing the length of the elongated passage through which liquid is flowed comprises a shunt for selectively bypassing the liquid about a portion of the elongated passage defined between the first surface of the metering member and the baffle member. According to the disclosed embodiment, the metering member and baffle member are secured against movement relative to one another in the device by bonding the two members together. At least one of the metering member and the baffle member has a plurality of spaced openings communicating with respective portions of the elongated passage defined between the members. The shunt is movable relative to the spaced openings to selectively communicate a bypass passage of the shunt with respective ones of the openings to thereby change the length of the elongated passage through which the liquid is flowed to the outlet of the device. In particular, the shunt is rotatable with respect to the assembly of the metering member and the baffle member to selectively communicate the bypass passage with respective ones of the openings in the one of the members formed with such openings. The elongated passage defined between the metering member and the baffle member extends in a serpentine shape in the illustrated embodiments. The shunt is fixed for rotation with a dial cover of the fluid dispensing device. The device further includes means permitting injection of a hypodermic needle into the device for introducing liquid into the reservoir of the device to initially fill the reservoir.

The constant force applied to the flexible reservoir in the fluid device of the invention causes a constant pressure on the liquid within the reservoir of the device. This results in a constant flow of liquid through the flow control means and outlet of the device with a given setting of the flow control means. Therefore, the device of the invention provides an inexpensive, lightweight, ambulatory disposable drug infusion pump which can be safely used in many medical applications including the administration of chemotherapy drugs for cancer patients, anticoagulant drug for patients with circulatory illnesses, pain reducing drugs for burn patients and patients with rheumatic diseases, insulin for diabetics, veterinary medicine applications, etc.

These and other objects, features and advantages of the present invention will become more apparent from the following description when taken in connection with accompanying drawings which show, for purposes of illustration only, two embodiments in accordance with the invention.

DETAILED DESCRIPTION OF THE DISCLOSED EMBODIMENTS

Referring now to the drawings, a fluid dispensing device 1 according to a preferred embodiment of the invention comprises a reservoir 2 for a liquid to be administered parenterally to a patient through an outlet 3 of the device as shown in FIGS. 1–4. The outlet 3 can be connected to an elongated flexible tube (not shown) for conveying the liquid from the outlet to the site for infusion in the patient as with a canula or catheter, for example, which is inserted into the cardiovascular system of the patient to introduce the liquid into the patient's system. The fluid dispensing device can be used in medical applications for administration of liquids such as chemotherapy drugs for cancer patients, anticoagulant drugs for patients with circulatory illnesses, pain reducing drugs for burn patients and patients with rheumatic diseases, insulin for diabetics, and veterinarian medicine applications.

The liquid drug to be administered parenterally to the patient is placed in the reservoir 2 of the device by injection through a distal septum 4 located centrally in an opening 5 in a dial cover 6 of the device as depicted in FIGS. 1–4. A shunt 7 in the form of a passageway is formed on the inside surface of the dial cover 6 of the device radially outwardly from the opening 5. The distal septum 4 allows passage of a hypodermic needle, shown schematically at 8 in FIG. 1, into the reservoir 2 for injecting liquid into the reservoir. The septum 4 is self-sealing so that after a physician fills the reservoir with a drug by injection using a hypodermic needle and the needle is removed from the septum, the septum then effectively seals the opening 5 in the dial cover against leakage through the opening or septum. A central aperture 9 extends through a metering plate 10, a baffle plate 11 and a housing member 12 of the device in alignment with the opening 5 and septum 4 in the dial cove to allow passage of the needle and injected liquid to the reservoir 2.

The reservoir 2 is formed of a flexible material such as synthetic rubber, by molding. It has an open end which is closed by the inner surface 13 of the housing member 12. More particularly, a flange 14 of the reservoir 2 is sealed to the periphery of the surface 13 of the housing member 12 as by adhesive bonding to form the liquid-tight reservoir. Ingress of liquid to the reservoir 2 is possible only through the central aperture 9 in the housing member 12, baffle plate 11 and metering plate 10 and the aligned opening 5 and septum 4 in the dial cover 6. The housing member 12 is preferably formed of a molded plastic material such as polysulfone. Egress of liquid from the reservoir is by way of a second aperture 15 in the housing member. A flow control means 16 is provided in fluid communication with the aperture 15 between the reservoir 2 and the outlet 3 of the device for adjustably controlling the flow rate of the liquid dispensed from the device. A mechanism 17 in the lower part of the device 1 is adapted to place the liquid in the reservoir 2 under a constant pressure for dispensing the liquid from the reservoir 2, through the flow control means 16 and from the outlet 3 of the device after the reservoir has been filled as discussed below.

The mechanism 17 comprises a compression spring 18 and a variable helix angle translator 19 which are positioned in the device 1 between a base housing 20 of the device and the lower surface of the flexible reservoir 2. The base housing 20 may be formed of molded plastic such as polysulfone. The variable helix angle translator 19 is preferably formed of a synthetic rubber material as by molding. The central upstanding portion of the translator 19 is relatively thin and flexible so that it can conform to the configuration of the reservoir 2 against which it is normally positioned. The surrounding flange 21 of the translator 19 is thicker to lend structurally stability to the translator. Three equiangularly spaced pins 22 protrude radially outwardly of the flange 21. These pins are received in corresponding slots 23 formed in the depending wall 24 of the housing member 12. The angular orientation of the slots 23 in the wall 24 varies in order to provide a constant axial force, that is, the slots are in the form of a variable helix so as to provide a constant axial load vector for compressing the reservoir 2 and in turn placing the liquid therein under constant pressure as the spring 18 extends.

Figure 1:
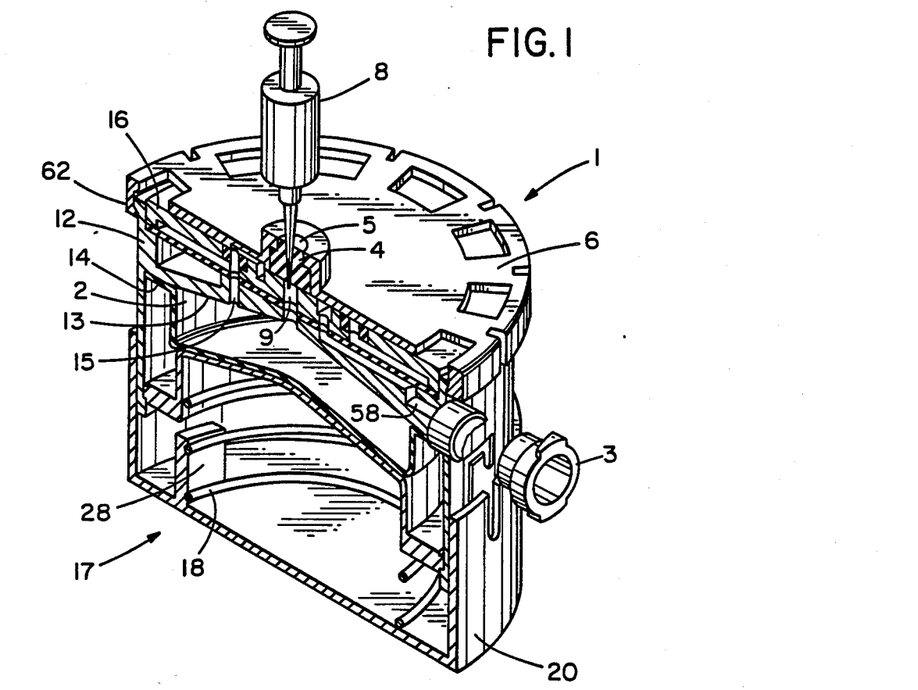
FIG. 1 is an elevational view from above and to one side of a cross sectioned fluid dispensing device according to a first embodiment of the invention wherein the flexible reservoir of the device is shown in its full position with a hypodermic needle being schematically illustrated in position for filling the reservoir.
Figure 2:
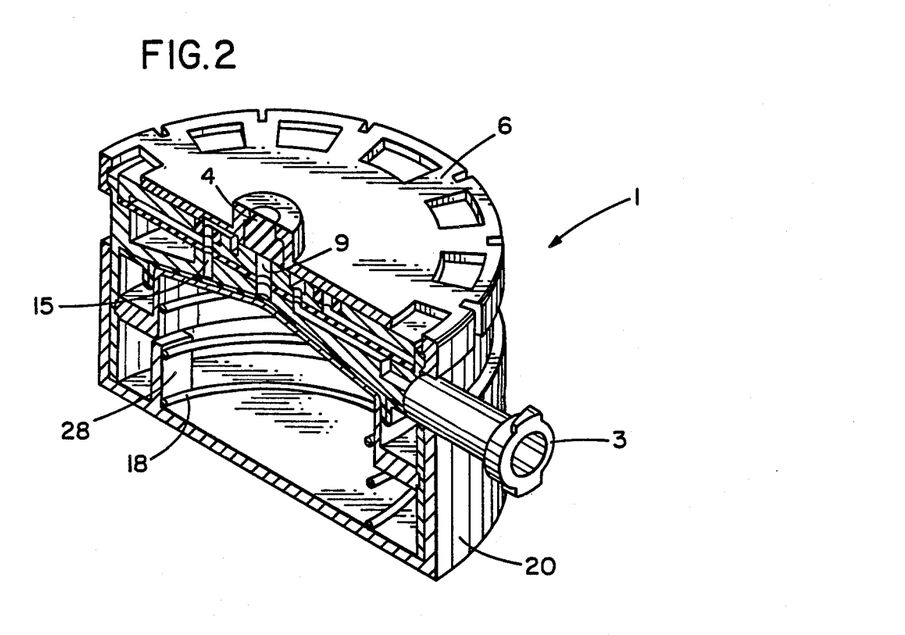
FIG. 2 is an elevational view of the device as shown in FIG. 1 wherein the flexible reservoir of the device is i its compressed, empty position.

More particularly, as the spring 18 extends to compress the reservoir 2 from its full position as shown in FIG. 1 to its empty position as shown in FIG. 2, the force applied by the spring decreases. However, the resistance provided by the helix angle of the slots 23 decreases proportionally in order to maintain a constant force against the reservoir 2, hence to maintain the liquid in the reservoir under a constant pressure throughout the discharge of liquid from the device 1. This permits a constant flow from the device for a given flow rate setting of the flow control means 16. The variable helix angle translator 19 is rotatable with respect to the depending wall 24 of the housing member 12 to permit movement of the pins 22 in the slots 23 as the reservoir 2 collapses during discharge of liquid therefrom.

The base housing 20 and the housing member 12 of the device 1 are initially positioned in assembled relation as shown in FIG. 1. Three pins 25 are provided on the inside of an upstanding flange 26 of the base housing 20. The pins 25 are received in adjacent recesses 27 formed in the outer peripheral surface of the depending wall 24 of the housing member 12. In the position shown in FIG. 1 the pins 25 ar located in the lower portion of one side of the recesses 27 in an "unloaded" position where the compression spring 18 does not urge the flexible reservoir 2 in a manner which applies pressure on any liquid in the reservoir. In this position the reservoir 2 can be easily filled through the distal septum 4 as discussed above.

Once the reservoir is filled, the upper portion of the device 1, including the housing member 12, is depressed and rotated clockwise slightly relative to the base housing 20 so as to position the pins 25 in the right side of the recesses 27 as shown in FIG. 1. This loads the compression spring 18 which, in turn, applies pressure on the reservoir 2 and the liquid therein through the translator 19 and the flexible wall of the reservoir. Liquid in the reservoir is then forced through the aperture 15 of the housing member 12 toward the flow control means 16 and outlet 3 of the device.

Compression springs of the same basic design can have a load rate tolerance which varies ±10%, for example, from one spring to another. To compensate for this, in order to achieve a predetermined force on the reservoir when the spring is loaded, three spring load adjusters 28 are provided on the base housing 20 to permit the compression spring 18 to be screwed into the adjusters of the base housing during assembly of the device until the desired load rate is attained. The compression spring is then cemented in position in the screw threads formed on the radially inward faces of the equiangularly spaced adjusters.

The flow control means 16 of the device 1 comprises means defining an elongated passage through which liquid from the reservoir 2 can be flowed to the outlet 3 of the device and means for changing the length of the elongated passage through which the liquid is flowed to thereby change the flow rate of the liquid through the passage where a constant pressure is applied to the liquid in the reservoir. More specifically, as illustrated in the patent drawings, a surface 29 of the metering plate 10 which faces the baffle plate 11 has a serpentine-shaped groove 30 formed therein. The groove can have a width of 0.025 inch and a depth of 0.015 inch, for example, and extends in serpentine fashion, circularly nearly completely around the flat, circular surface 29. The central aperture 9 also extends through the surface 29. Eleven radially inwardly extending branches 31–41 of the groove 30 are equiangularly spaced around the central aperture 9 with the exception that the angular spacing between the branch 31 and branch 41 is twice that of the spacing between the other branches. Eleven through passages or openings 43–53 are provided in a concentric array in the baffle plate 11 about aperture 9 in communication with respective ones of the branches 31–41.

Figure 3:
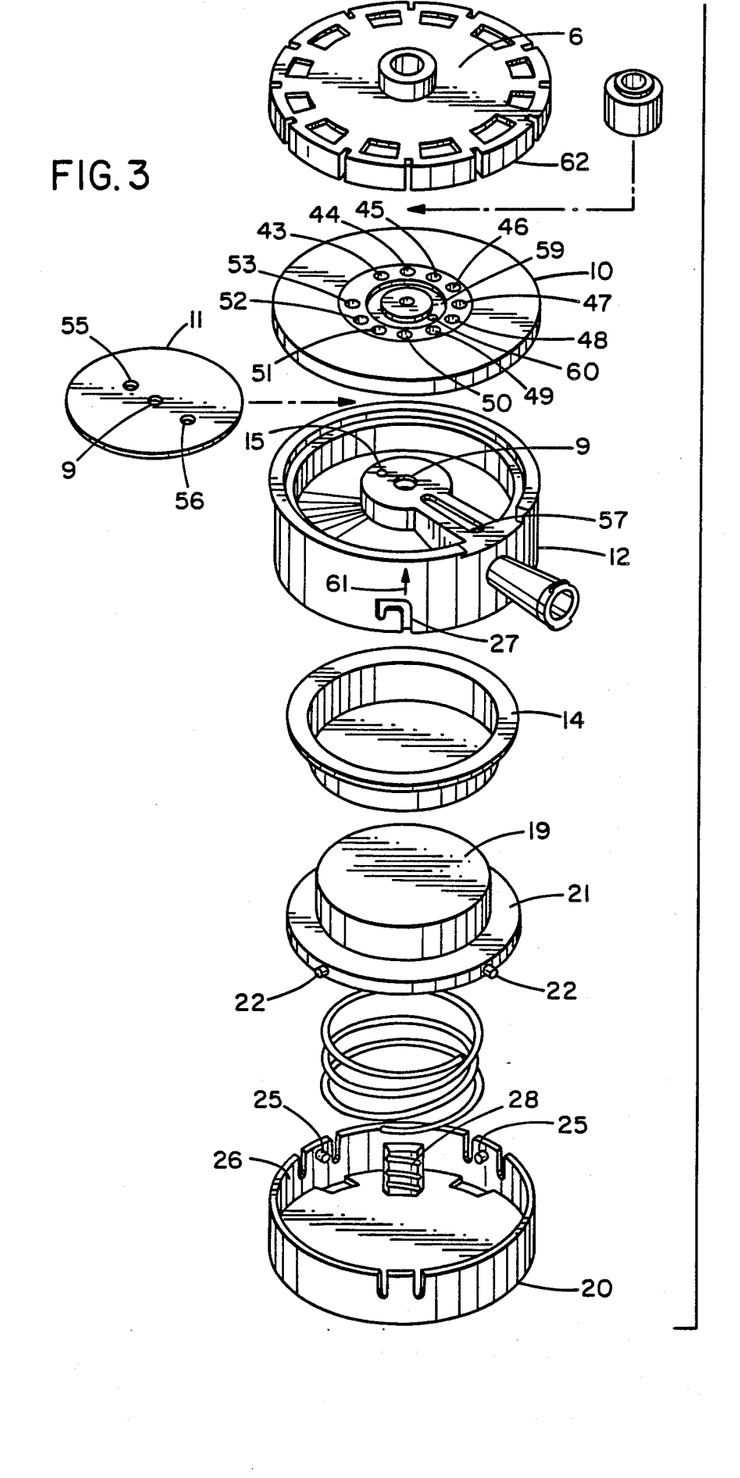
FIG. 3 is a side elevational view of the entire fluid dispensing device of FIGS. 1 and 2 with the various components thereof being shown in disassembled relation to one another.
Figure 4:
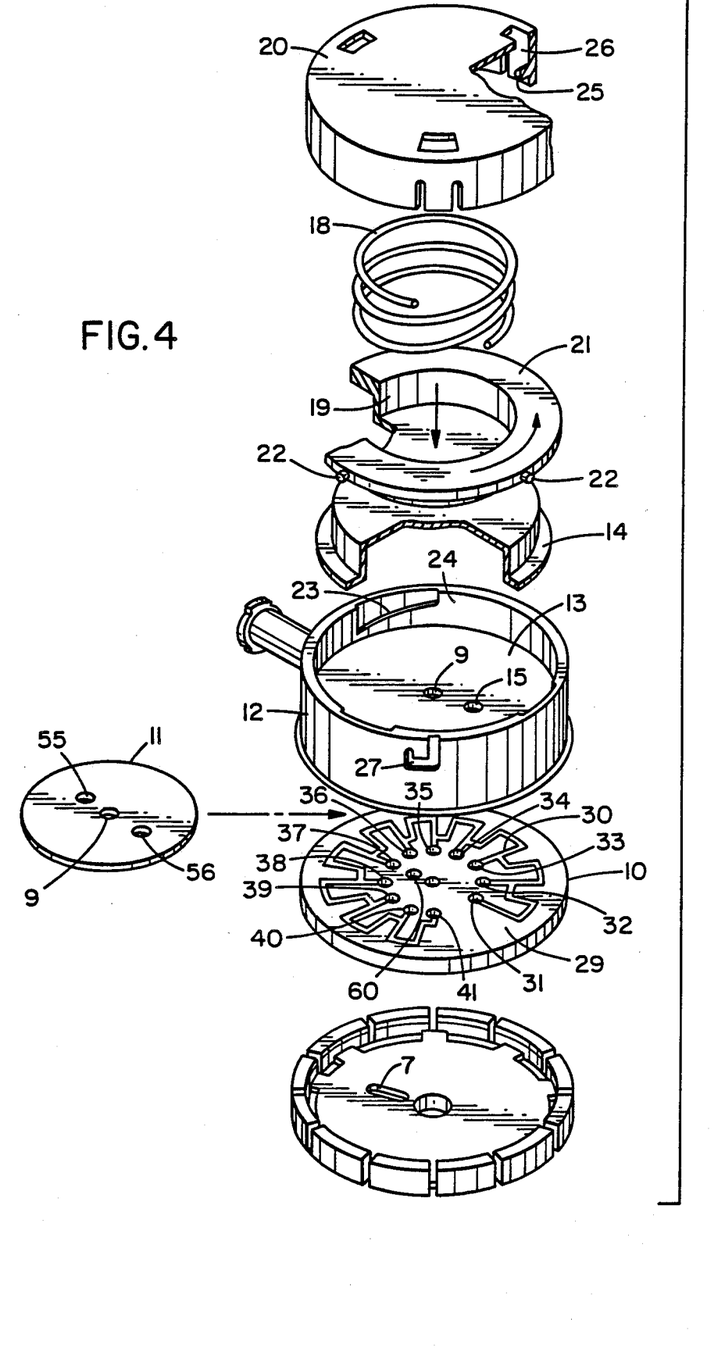
FIG. 4 is a side elevational view of the entire fluid dispensing device of FIGS. 1 and 2 like that of FIG. 3 except that the device is shown disassembled in its inverted position, so that the opposite sides of the component parts shown in FIG. 3 are visible.

The baffle plate 11 of the flow control means 16 of the device 1 is a thin, flat circular member with essentially the same outer diameter as the surface 29 of the metering plate 10. The baffle plate 11 is formed with three passages therethrough as shown in FIG. 3. One of the passages is the centrally located aperture 9, a second passage 55 is adapted for alignment with the aperture 15 in the housing member and the opening 43 of the metering plate 10, and the third passage 56 is for positioning over a relatively large, radially extending groove 57 formed in the surface of the housing member 12 facing the baffle plate 11 and communicating with outlet 3. The groove 57 can have a width of 0.10 inch and a depth of 0.10 inch, for example, so as to offer little resistance to the flow of liquid therethrough. The radially outer end of the groove 57 is in communication with the outlet 3 by a passage 58 through the housing member 12 as shown in FIGS. 1 and 2.

The baffle plate 11 is in the form of a thin film of 0.007 inch thick polyester with 0.001 inch of pressure sensitive acrylic on both sides, in the disclosed embodiments. The plate 11 is preferably adhesively bonded to the surface 29 of the metering plate 10 to form the serpentine-shaped elongated passage for the liquid from the reservoir 2. The baffle plate 11 and the adjacent surface of the housing member 12 are also preferably bonded to one another as by adhesives, for example. In the assembled condition, the housing member 12, baffle plate 11 and metering plate 10 are secured against movement relative to one another as a result of their bonded surfaces. The bonded surfaces of the baffle plate, the housing member and the metering plate form liquid tight seals about the passages.

The shunt 7 is in the form of a radially extending passageway on the inner surface of the dial cover 6. The inner surface of the dial cover is molded against a flat polished surface, so that it is sufficiently flat to form a seal against the adjacent surface of the metering plate 10 in the assembled condition of the device 1 while being rotatable with respect to the metering plate. The depth and width of the radial passageway of the shunt 7 can be 0.050 inch. The shunt 7 and the cooperating surface of the metering plate 10 in the assembled condition form a passage for liquid flow from one of the eleven openings 43–53 in communication with the serpentine-shaped groove 30. Liquid exiting from the groove 30 is conveyed with little resistance through the shunt 7 to an annular channel 59 formed in the surface of the metering plate 10 adjacent the dial cover. Liquid in the channel 59 flows to an outlet opening 60 in the channel 59 of the metering plate and then through the mating aperture or passage 56 in the baffle plate 11 to the groove 57 in the housing member and on to the passage 58 to the outlet 3.

In a position corresponding to an ON or high flow rate position of the flow control means, liquid is forced at a relatively high flow rate from the reservoir 2 through the outlet to the patient since all of the serpentine-shaped passage is bypassed. Rotation of the shunt 7 and dial cover 6 to one of the other settings incrementally changes the length of the serpentine-shaped passage through which the liquid must flow thereby changing the flow rate of the liquid from the outlet 3 under the condition of a constant pressure on the reservoir. In the OFF position, the shunt 7 is located in the space on the metering plate 10 where there is no aperture. Thus, by adjustably positioning the shunt 7 and dial cover 6, various, incremental changes in the length of the flow passage through the device can be made to thereby incrementally adjust the flow rate of liquid from the device 1. Once set, the flow rate will remain constant because the pressure on the liquid in the reservoir remains contant. Alignment of respective indicia provided about the periphery of the dial cover 6 with an arrow 61 provided on the housing member 12 indicates proper alignment of the shunt 7 with one of the passages in the metering plate 10. The dial cover 6 is rotatably secured on the housing member 12 at its flange 62. Typical flow rates which can be set with the device are 24 ml/day in the ON position with flow rates being reduced 2 ml/day per increment of increase in the length of the flow path, e.g., with each additional setting of the dial cover indicia relative to the arrow 61. Higher or lower flows and incremental variations therefrom could be achieved by altering passage dimensions as will be readily apparent to the skilled artisan.

In use, the fluid dispensing device of the invention as shown in FIG. 1 is first filled with a liquid containing a drug to be administered parenterally to a patient. Once the hypodermic needle is removed from the device, the compression spring 18 of the device is loaded by depressing the housing member 12 and rotating it counterclockwise relative to the base housing 20 to compress and set the compression spring for maintaining pressure against the flexible reservoir 2. The dial cover is then set in the appropriate position with respect to the arrow 61 for the desired liquid flow rate from the outlet 3. Liquid will be dispensed through the outlet 3 of the device at the predetermined, controlled rate until the reservoir 2 is emptied as the variable helix angle translator 19 together with the compression spring 18 maintain a constant force against the reservoir 2 as it collapses. The low number of parts and the small size of the fluid dispensing device 1 of the invention result in an inexpensive, light-weight, ambulatory disposable drug infusion pump with wide application as discussed above.

In the embodiment of the invention illustrated in FIGS. 5-8, the fluid dispensing device 63 is like that in the embodiment of that in FIGS. 1-4 except for the means for placing the liquid in the reservoir under a constant pressure for dispensing the liquid from the device. In the device 63, a constant load negator type spring 64 is employed instead of a compression spring as in the embodiment of FIGS. 1-4. One end 65 of the spring 64 is secured against rotational movement in the device 63 in a mount 66 therefor in the base housing 67 of the device. The other end 68 of the spring is secured in a mount 69 of a torque transmitter 70.

Figure 5:
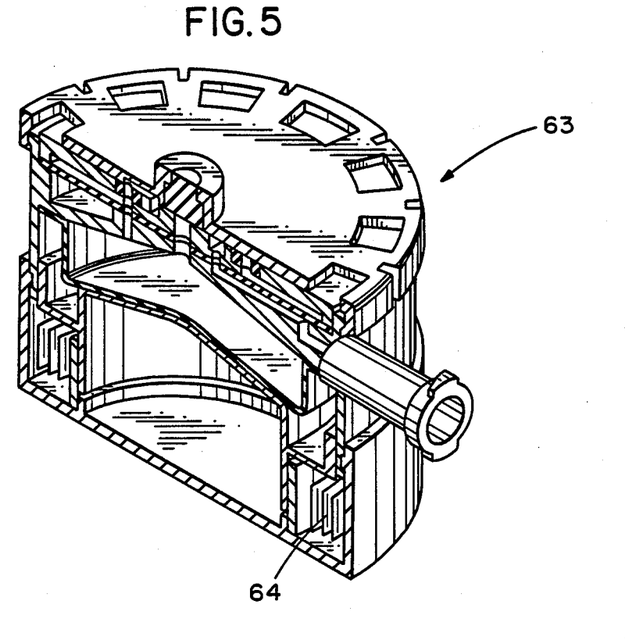
FIG. 5 is an elevational view from above and to one side of a cross-sectioned fluid dispensing device according to a second embodiment of the invention wherein the flexible reservoir of the device is in its full position.
Figure 6:
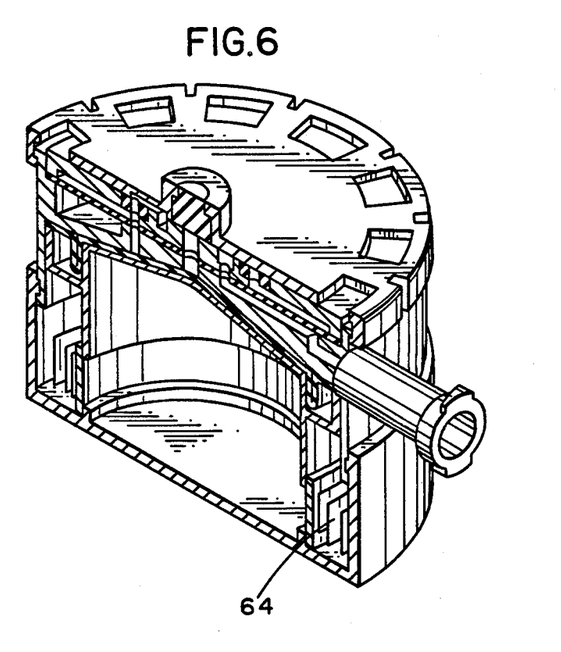
FIG. 6 is an elevational view of the device as shown in FIG. 5 wherein the flexible reservoir of the device is in its compressed, empty position.
Figure 7:
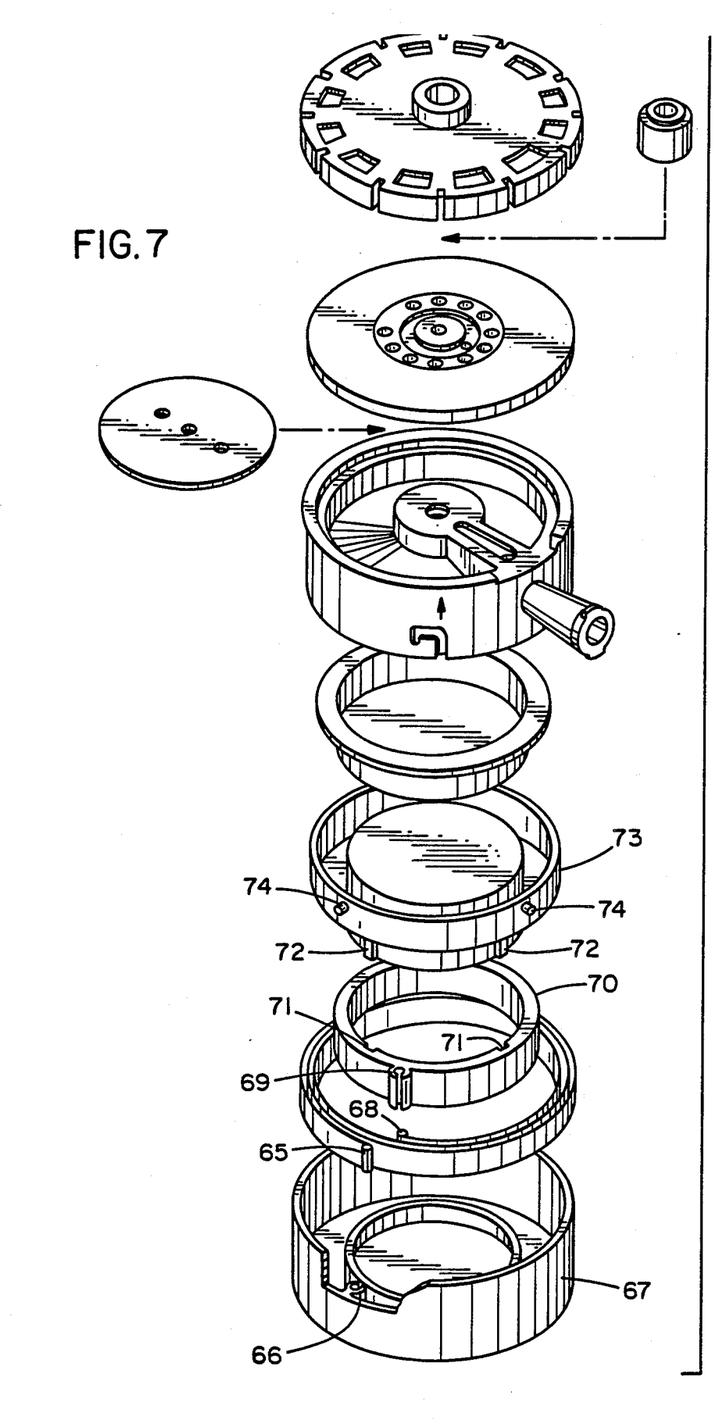
FIG. 7 is a side elevational view of the fluid dispensing device of FIGS. 5 and 6 with the various components of the device being shown in disassembled relation to one another.
Figure 8:
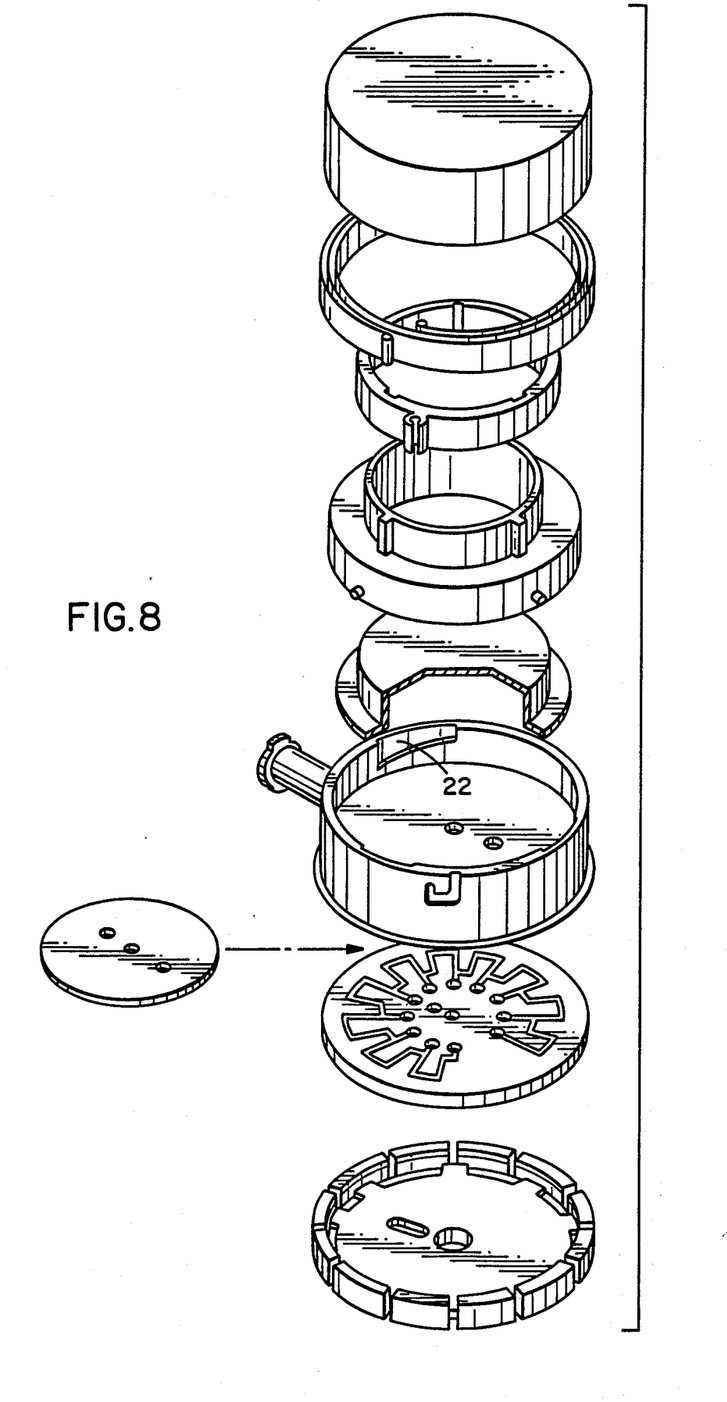
FIG. 8 is a side elevational view of the entire fluid dispensing device of FIGS. 5 and 6 like that of FIG. 7 except that the device is shown disassembled in its inverted position so that the opposite sides of the component parts shown in FIG. 7 are visible.

The torque transmitter 70 is ring-shaped and is formed with a pair of keyways 71 on the inner surface thereof for receiving keys 72 provided on a lower annular portion of a radial to axial translator 73. The translator 73 is formed with three pins 74 on its outer periphery. The pins 74 are received in respective slots 23 formed on the inner surface of the annular housing member 12. The slots 23 are in the form of a constant helix in the lower portion thereof for converting the radial force of the negator spring into axial force via the radial to axial translator 73. The translator 73 in turn is positioned against the flexible reservoir 2. The full and empty positions of the reservoir are illustrated in FIGS. 5 and 6 of the drawings.

The operation of this device is essentially the same as the device 1 in the embodiment of FIGS. 1-4 in that the device 1 is initially arranged as shown in FIG. 1, so that the spring 64 is not loaded. After the reservoir 2 is filled with liquid, the spring 64 is loaded by depressing and rotating the housing member 12 relative to the base housing 67 in order to move the pins 74 to the lower portion of the slots 22. The radial force of the loaded spring is then transmitted as axial force to the reservoir through the torque transmitter 70 and the radial to axial translator 73 for maintaining a constant force against the reservoir and the liquid therein. This insures a constant flow rate from the device for a given setting of the flow control means 14 in the manner discussed above.

While I have shown and described only two embodiments in accordance with the present invention, it is understood that the same is not limited thereto, but is susceptible of numerous changes and modifications as known to those skilled in the art. Therefore, I do not wish to be limited to the details shown and described herein, but intend to cover all such changes and modifications as are encompassed by the scope of the intended claims.

I claim:

1. An ambulatory fluid drug dispensing device comprising a reservoir for a liquid to be administered parenterally to a patient, means for introducing liquid in the reservoir, means for placing the liquid in the reservoir under constant pressure for dispensing the liquid from the device, said means for placing including a spring for applying a constant force to the liquid in the reservoir and means for tensioning said spring to initially apply the constant force on the liquid in the reservoir after the liquid has been introduced in the reservoir and flow control means for adjustably controlling the flow rate of the liquid dispensed from the device, said flow control means comprising means defining a elongated passage through which liquid from said reservoir can be flowed to an outlet of said device and means for changing the length of said elongated passage through which the liquid is flowed to thereby change the flow rate of the liquid through the passage.

2. A fluid dispensing device according to claim 1, wherein at least a portion of said reservoir is formed of a flexible material to allow the reservoir to be compressed to place the liquid therein under pressure.

3. A fluid dispensing device according to claim 2, wherein said means for placing the liquid in the reservoir under a constant pressure presses the flexible material of said reservoir to place the liquid therein under said constant pressure.

4. A fluid dispensing device according to claim 1, wherein the spring of said means for placing the liquid in the reservoir under a constant pressure is a compression spring and wherein a variable helix angle translator is interposed between said compression spring and said reservoir, so that a constant force can be applied to the liquid in said reservoir as the compression spring extends in order to maintain said constant pressure on the liquid in said reservoir.

5. A fluid dispensing device according to claim 4, wherein said device includes means for adjusting the load rate of said compression spring at least during assembly of said device.

6. A fluid dispensing device according to claim 1, wherein said spring is a constant load negator type spring and further including means translating a radial force of said spring into axial force for application to the liquid in said reservoir.

7. A fluid dispensing device according to claim 1, wherein said means defining an elongated passage includes a metering member having an elongated groove with a small cross-sectional area formed in a first surface thereof and a baffle member having a surface overlying said groove, and wherein said means for changing the length of said elongated passage through which said liquid is flowed comprises a shunt having means for selectively bypassing said liquid about at least a portion of the elongated passage defined between the first surface of said metering member and said baffle member through a bypass passage.

8. A fluid dispensing device according to claim 7, wherein said metering member and baffle member are secured against movement relative to one another in said device.

9. A fluid dispensing device according to claim 8, wherein said metering member and said baffle member are bonded to one another.

10. A fluid dispensing device according to claim 7, wherein that portion of the elongated passage formed by the elongated groove in the metering member and the overlying surface of the baffle member has a cross-sectional area on the order of $5 \times 10^{-4}$ inch$^2$ or less.

11. A fluid dispensing device according to claim 7, wherein at least one of said metering member and said baffle member has a plurality of spaced openings communicating with respective portions of said elongated passage defined between said members, said shunt being movable relative to said spaced openings to selectively communicate said bypass passage with respective ones of said openings to thereby change the length of the elongated passage through which said liquid is flowed.

12. A fluid dispensing device according to claim 11, wherein said shunt is rotatable with respect to said one of said metering member and said baffle member provided with said openings to selectively communicate said bypass passage with respective ones of said openings.

13. A fluid dispensing device according to claim 7, wherein the elongated passage defined between said metering member and said baffle member extends in a serpentine shape.

14. A fluid dispensing device according to claim 7, wherein said shunt is fixed for rotation with a dial cover of said dispensing device.

15. A fluid dispensing device according to claim 7, wherein a means is provided for permitting injection of a hypodermic needle into said device for introducing liquid into the reservoir of said device.

16. An ambulatory fluid drug dispensing device comprising a flexible reservoir for liquid to be administered parenterally to a patient, a spring for placing the liquid in said reservoir under a constant pressure for dispensing said liquid from the device, means for introducing liquid in said reservoir, means for tensioning said spring after introduction of liquid in the reservoir to apply said constant pressure to the liquid which has been introduced into said reservoir and flow control means for adjustably controlling the flow rate of the liquid dispensed from the device.

* * * * *